United States Patent [19]

Lee et al.

[11] Patent Number: 5,585,467
[45] Date of Patent: Dec. 17, 1996

[54] PROTEOGLYCAN(G009) EFFECTIVE IN ENHANCING ANTITUMOR IMMUNITY

[75] Inventors: Kwon H. Lee; Hoon Chung; Choon W. Lee; Chun H. Chung, all of Seoul, Rep. of Korea

[73] Assignee: Il-Yang Pharmaceutical Co., Ltd., Seoul, Rep. of Korea

[21] Appl. No.: 66,162

[22] PCT Filed: Dec. 4, 1991

[86] PCT No.: PCT/KR91/00031

§ 371 Date: Aug. 4, 1993

§ 102(e) Date: Aug. 4, 1993

[87] PCT Pub. No.: WO92/10202

PCT Pub. Date: Jun. 25, 1992

[30] Foreign Application Priority Data

Dec. 4, 1990 [KR] Rep. of Korea .................. 90-19876

[51] Int. Cl.$^6$ ............... A61K 35/70; C07K 14/37
[52] U.S. Cl. ............... 530/395; 530/322; 435/71.2; 435/70.1
[58] Field of Search ............... 530/395, 322; 435/71.7, 71.2

[56] References Cited

PUBLICATIONS

Lee et al., "Pharmacological, Toxicological Studies of Antitumor Polyaaccharides Obtained from *Ganodmora lucidum* IH 009", Kor. J. Appl. Microbiol. Technol. vol. 22 (2) pp. 182–89 (1994) pp. 182 & 187 Applied as Exhibit A.
Shimura et al, Japan J. Pharmacol., vol. 33, pp. 403–408 (1983).
Suzuki et al, Chem. Pharm. Bull., vol. 37(2), pp. 410–413 (1989).

*Primary Examiner*—Christina Y. Chan
*Assistant Examiner*—Lynn Touzeau
*Attorney, Agent, or Firm*—Birch, Stewart, Kolasch & Birch, LLP

[57] ABSTRACT

This invention relates to a proteoglycan G 009 possessed of antitumoral and immunostimulating effects, and separated from the cultured *Ganoderma lucidum* (KFCC-10709), containing:

β-glucose, α-glucose, galactose, α-mannose and fructose as saccharide components, and glycine, alanine, histidine, arginine, valine, aspartic acid, threonine, isoleucine, serine, leucine, glutamic acid, tyrocine, proline, phenylalanine and methionine as protein components.

8 Claims, 4 Drawing Sheets

PROTEOGLYCAN(G009) EFFECTIVE IN ENHANCING ANTITUMOR IMMUNITY

DETAILED DESCRIPTION OF THE INVENTION

The present invention relates to a proteoglycan effective for promotion of antitumor immunity.

In order to search for a new proteoglycan which has the effect of promotion antitumor immunity, the present inventors collected a large number of basidiomycetes and attempted to separate a proteoglycan produced by those basidiomycetes. In sequel thereto, it was found that the basidiomycete which belongs to the genus of ganoderma, picked up in the area of the Dooryoon Mountains located in the South Cholla Provine, produces a proteoglycan which has the effect of promoting antitumor immunity when cultured in a proper culture medium. After the produced proteoglycan was separated and its physicochemical and biophysical properties was examined, it was designed as proteoglycan G009 which has the effect of promoting antitumor immunity and the strain which produces it was designated as *Ganoderma lucidum* IY 009 (a number of deposition to the Korean Species Association is KFCC-107090 dated Oct. 5, 1990).

Although researches have been conducted in such medicinal components as antibacterial, hallucinative, toxicant and cholesterol-lowering components from the basidiomycetes belonging to a higher fungus, earnest study is now given to an antitumor component and an immunity improvement action, and so basidiomycetes are rising in importance. Thus, those strains which secrete such matter as contains an antitumor component and improves an immunity function was separated and cultured in liquid to make a study of its pharmacological effect.

During the study, a mutant strain which has an antitumor effect and an immunity improvement function that are more excellent than the species belonging to the genus of Ganoderma which has been identified until now was separated and an in-liquid mycelia culture method was established and then the antitumor effect and immunity improvement function of those components extracted from the cultured mycelia were confirmed.

The present invention will now be described in detail according to the following embodiment and experimental examples.

EXAMPLE 1

Separation of proteoglycans

1) Strain:

The *Ganoderma lucidum* starins were collected in the area of the Dooryoon Mountains located in the South Cholla Province and identified.

2) Preserved culture medium:

An inclined culture medium for potato dextrose agar (PDA); 39 g of potato dextrose culture medium (Difico, USA) was made in to 1 liter by dissolving it in distilled water and it was made into an inclined culture medium after high-pressure sterilization for 20 minutes at 121° C.

A culture medium for in-liquid culture:

50 g of glucose, 20 g of peptone, 0.87 g of $KH_2PO_4$, 0.5 g of $MgSO_4 \cdot 7H_2O$, 10 mg of $FeCl_2 \cdot 6H_2O$, 7 mg of $MnCl_2 \cdot 4H_2O$, 10 mg of $ZnSO_2 \cdot 5H_2O$ and 4 mg of $ZnCl$ were made into 1 liter by adding distilled water thereto. It was sterilized for 20 minutes at 121° C. by adjusting the pH value to 5.5.

3) Culture:

The strains kept in custody were transplanted into the inclined culture medium for PDA and grown for 7 days at 25°±1° C. Then, the grown mycelia were separated in an aseptic way and put into 100 ml of culture medium for in-liquid culture and triturated with a microblender for 15 seconds. It was moved into a 500 ml-triangular flask and shake-cultured for 10 days until the mycelium formed a mature mycetome with a diameter of about 5 mm by 180 rpm at 25°±1° C.

After the mycetome was triturated with a microblender for 10 seconds, it was inoculated 5% (V/V) by 5% into a 500 ml-triangular flask containing a 100 ml-culture medium for in-liquid culture and shake-cultured for 10 days under the same conditions as stated above.

The cultured mycelia were made into species by triturating them again for 10 seconds and the 100 ml-culture medium for in-liquid culture was put into the 500 ml-triangular flask and the species was inoculated thereinto 5% by 5%. Then, it was shake-cultured by 170 rpm for 7 days in an orbital shaker (the radius of revolution: 1 inch, Vision Science Co.) at 25°±1° C.

4) Extraction and separation of proteoglycans

After the whole of culture-conditioned solution was centrifugally separated for 15 minutes at 6000 rpm, only mycelia were taken and digested into a twofold 2.5N NaOH solution. It was left as it was for 24 hours at room temperature and centrifugally separated for 15 minutes at 6000 rpm. After the supernatant solution was neutralized to pH 7.4 with glacial acetic acid, it was dialyzed for 3 days with a visking tube (Sigma, USA). After dialysis, it was concentrated and twofold ethanol was added thereto. After it was left as it was for 24 hours at 4° C., it was centrifugally separated by 6000 rpm for 15 minutes and a precipitate was obtained therefrom. The precipitate was dissolved in deionized water and again centrifuged for 1 minute at 6000 rpm. The Supernatant was concentrated by vacuum evaporation and a proteoglycan was separated therefrom by lyophilizing the concentrated solution.

5) Purification of proteglycan 12.5 g of precipitate taken after the above sample was dissolved in water and excessive ethanol was added thereto was dissolved in water again. After this sample solution was applied to DEAE-cellulose (C1-form) column (3 cm×60 cm), it was centrifugally separated by adding the same amount of methanol to 200 ml of elution fraction obtained by elution with water and G1 (2.1 g) was obtained by washing the precitate in ethanol and dessicating it under reduced pressure. G2 (0.42 g) was obtained by the decompressed dessication of a precipitate obtained after a supernatant solution (400 ml) was centrifugally separated by adding 400 ml of ethanol thereto. G3 (1.1 g) was obtained by the decompressed essication of a precipitate obtained after a supernatant solution (400 ml) was centrifugally separated by adding ethanol (800 ml) again to the supernatant solution (800 ml) remaining after G2 was removed.

G1 was eluted with by dissolving it in water and applying it to Sephadex G-100. G4 (1.5 g) was obtained by lyophilizing the fraction of a tube No. 25–33 and separated by the decompressed dessication of G5 (0.5 g) including the fraction of a tube No. 34–44. After G4 was dissolved in water and the same amount of a solution mixed in the same amount was added to 0.15M cetavelon (cethytrimethyl ammonium bromide) and 0.1M borate buffer (pH 8.0), a precipitate (G7) and a supernatant solution (G6) were taken by adjusting pH to 9.0 with 0.5M NaOH. After G7 was dissolved in water by adding 2M glacial acetic acid, a precipitate was obtained by adding twofold methanol. After the precipitate was washed in methanol and aceton, it was dessicated under reduced pressure (G8). After G8 was applied to Sepharose C1–4B by dissolving it in small amount of water, it was eluted with water and G9 was obtained from a tube No. 25–30. G10 was obtained from the tube No. 31–46.

Experiment 1

Anticancer test

A test of the fraction obtained as above for antitumor activity against sarcoma-180 cells was conducted as follows:

Sarcoma-180 cells were transplanted at intervals of one week into the abdominal cavities of 20–25 g ICR male mice and these successively transferred sarcoma-180 cells were used as experimental tumor cells.

The sarcoma-180 cells cultured for 7 days in the abdominal cavities of those mice were taken together with abdominal ascites and centrifically separated for 5 minutes by 400 rpm after a sterile saline solution chilled with ice and was added thereto, and a precipitate of cells was separated.

The separated cells were washed in a physiological saline solution three times and diluted so as to attain $1 \times 10^7$ cells/mg. 0.1 ml of this cell suspension was transplanted by a hypodermic needle into the left inguinal regions of a group of 10 mice.

Proteoglycans, which are purified fractions, were administered to those mice for 10 consecutive days 72 hours after tumor cells were transplanted. A physiological saline solution was administered to the control group and the proteoglycans dissolved in a physiological saline solution was administered to the test group 0.1 ml by 0.1 ml by concentrating it to 20 mg/kg.

On the 30th day after transplantation of tumor cells, those mice were killed and the induced solid cancer was extracted. Then, average tumor weight was found by measuring its weight and percent tumor inhibition ratio was calculated according to the formula given below.

$$I.R. \% = \frac{CW - TW}{CW} \times 100$$

I.R.=Percent inhibition ratio
CW=Average tumor weight of control group
TW=Average tumor weight of test group As the result of an antitumor experiment conducted with sarcoma-180 cells, G9 which was found most excellent in the control group as shown in Table 1 was found and designated as G009. Analysis thereof was made in the following experiments.

TABLE 1

Anticancer effects produced by proteoglycan mice into which sarcoma-180 cells were transplanted

| proteoglycan | average weight of tumors(g) (Mean ± S.E) | inhibition ratio(%) |
| --- | --- | --- |
| control | 4.66 ± 0.17 | |
| G1 | 1.43 ± 0.25 | 69.3 |
| G2 | 3.54 ± 0.36 | 24.1 |
| G3 | 3.46 ± 0.39 | 25.7 |
| G4 | 1.05 ± 0.17 | 77.4 |
| G5 | 1.83 ± 0.29 | 60.7 |
| G6 | 1.62 ± 0.10 | 65.2 |
| G7 | 0.64 ± 0.22 | 86.2 |
| G8 | 0.43 ± 0.21 | 90.7 |
| G9 | 0.17 ± 0.09 | 96.3 |
| G10 | 1.40 ± 0.17 | 69.9 |

For chemical analysis of G009, the aggregate amount of saccharide was measured by Anthrone's color developing method and protein content was measured by Lowry et al's method. Then, amino acid and saccharide were analyzed.

Figure 1:
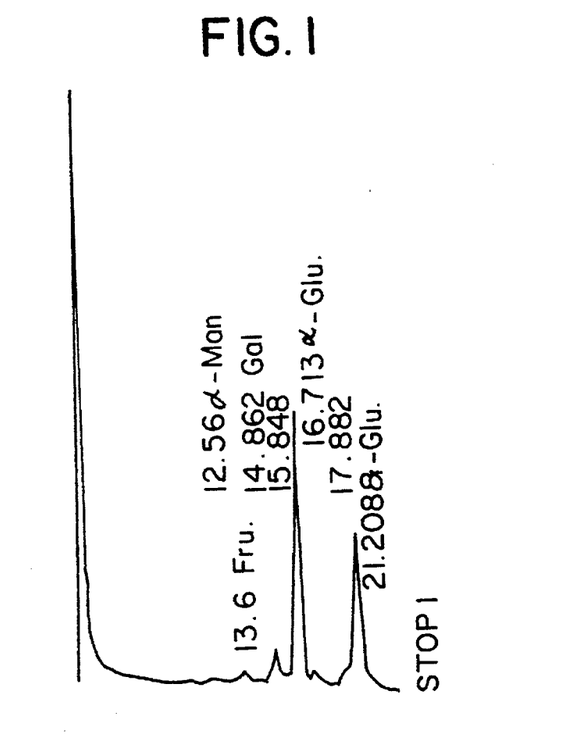
FIG. 1 is a saccharide analysis chromatogram of proteoglycan G009 according to the present invention.
Figure 2:
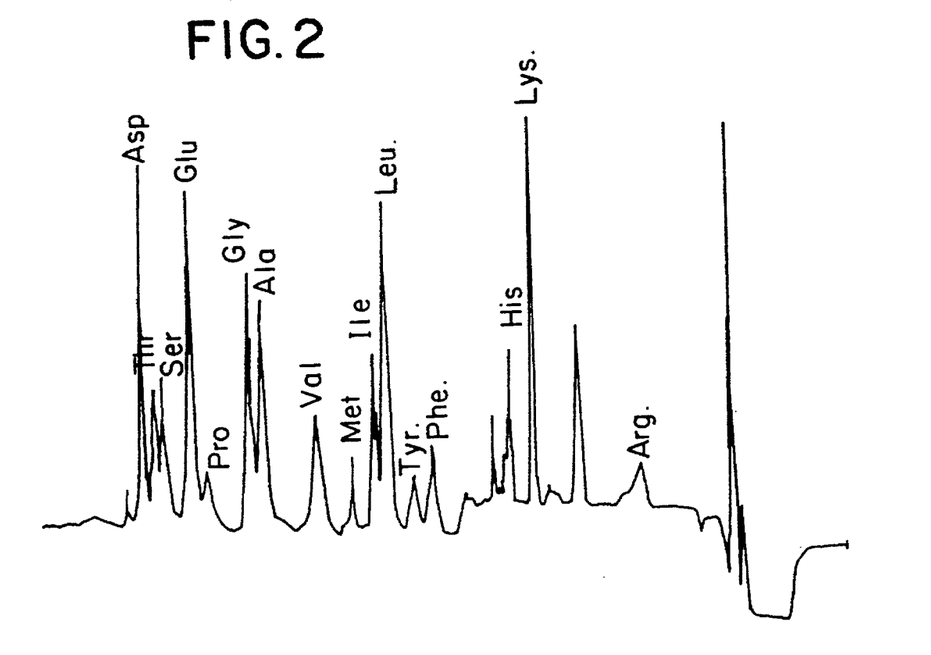
FIG. 2 is an amino acid chromatogram of proteoglycan G009 according to the present invention.
Figure 3:
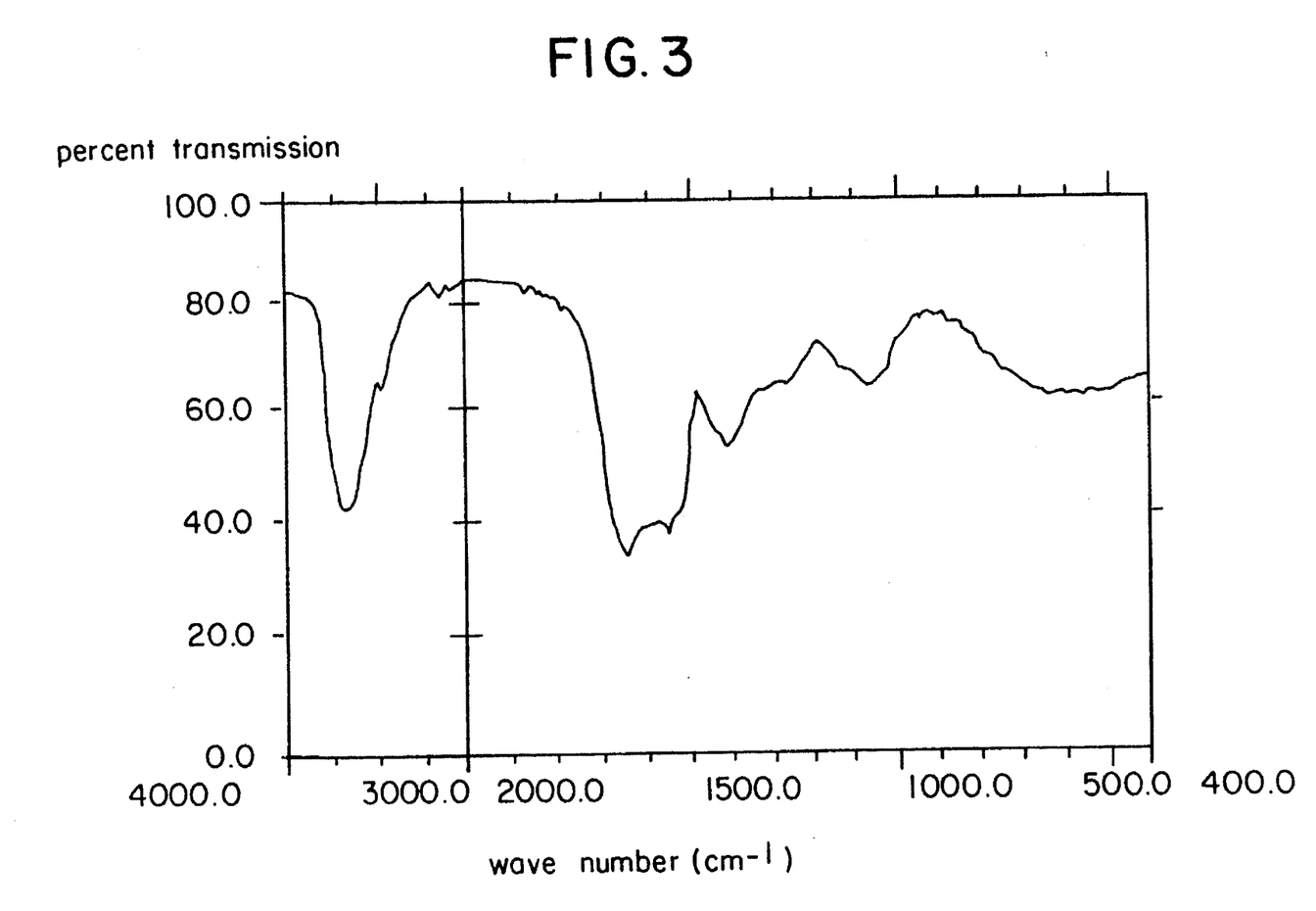
FIG. 3 is an IR analysis diagram of proteoglycan G 009 according to the present invention.
Figure 4:
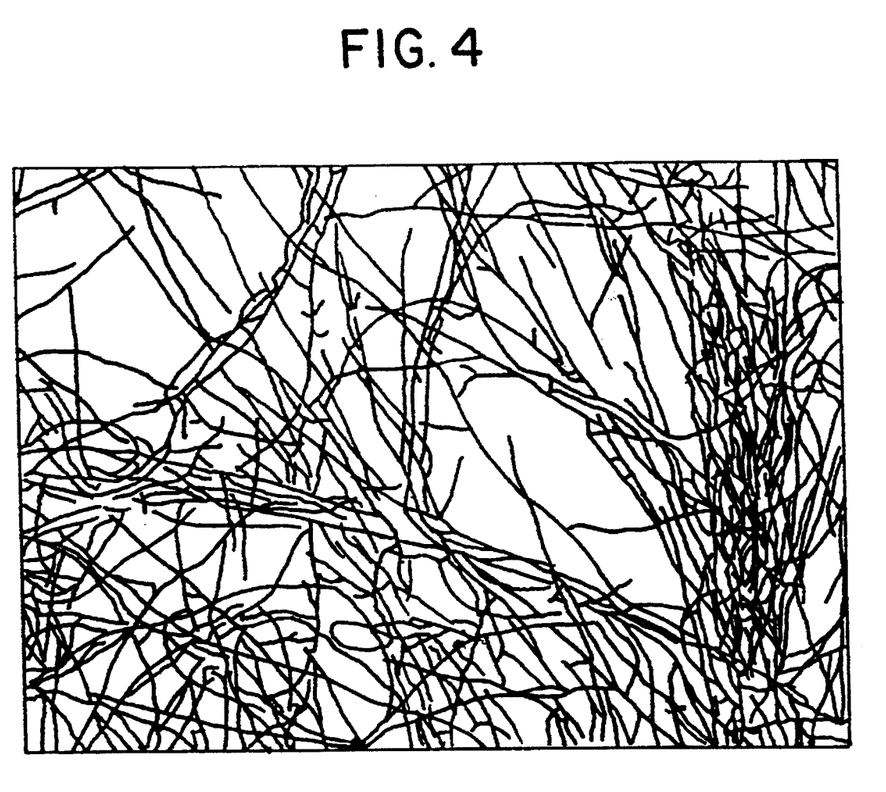
FIG. 4 is a microphotograph showing the mycelia of a strain IY 009 according to the present invention.

Results thereof are shown in Tables 2, 3 and 4. A saccharide chromatogram is shown in FIG. 1. An amino acid chromatogram is shown in FIG. 2 and I.R a analysis is shown in FIG. 3.

G.L.C. (Shimadzu GC 9A, Japan) use requirements for analysis of saccharide:

Column 3% OV-17 (80–100) (mesh shimalite)
3 mm$\phi$×1 boronsilicate glass column
Temperature Column 150°–180° C. Gradient, Detector 190° C.
Flow rate $N_2$: 50 ml/min
$H_2$: 60 ml/min (0.6 kg/cm$^2$)
Air: 60 ml/min (0.6 kg/cm$^2$)
Attenuation $10^2 \times 2^1$ a.f.s (ampere full scale)

TABLE 2

Total contents of polysaccharide and protein in G009

| Total content | polysaccharide (%) | protein (%) |
| --- | --- | --- |
| G 009 | 93 | 5 |

TABLE 3

Content of monosaccharide in the polysaccharide part of G 009.

| monosaccharide | Relative ratio(%) |
| --- | --- |
| α-glucose | 45.84 |
| β-glucose | 41.70 |
| galactose | 8.03 |
| α-mannose | 3.32 |
| fructose | 1.11 |

* Requirements for use of amino acid autoanalyzer (Beckman Sys. 6300, USA):

| Column | 2.6 × 200 mm |
| --- | --- |
| Ion exchange resin | #338076(Beckman) |
| Flow rate | Buffer solution  0.33 ml/min |
| | Ninhydrin  0.17 ml/min |
| Analysis cycle time | 60 min |
| Column pressure | 2100 psi(147 Kg/cm$^2$) |

-continued

| | |
|---|---|
| Ninhydrin pressure | 100 psi(7 Kg/cm²) |
| Column temperature | 50–70° C. Gradient |
| N₂ gas pressure | 40 psi |
| Reaction bath temperature | 130° C. |
| Wave length | 570 nm, 440 nm |

TABLE 4

Total amino acid content in the protein part of G 009.

| Amino acids | μmol/ml | Amino acids | μmol/ml |
|---|---|---|---|
| Gly | 8.070 | Ile | 3.499 |
| Lys | 4.133 | Ser | 2.066 |
| Ala | 7.072 | Leu | 5.973 |
| His | 1.469 | Glu | 11.031 |
| Thr | 3.191 | Tyr | 1.638 |
| Arg | 0.796 | Pro | 6.446 |
| Val | 5.800 | Phe | 2.316 |
| Asp | 9.435 | Met | 0.938 |

Experiment 2

A variation of antitumor effects according to G009 administration routes

G 009 was transplanted into the abdominal cavities of 20–25 g ICR male mice at intervals of one week and sarcoma-180 cells were used as experimental cells. The sarcoma-180 cells cultured for 7 days in the abdominal cavities of those mice were taken together with abdominal ascites. It was centrifugally separated at 3000 rpm for 5 minutes after adding a sterile saline solution chilled with ice thereto and a precipitate of cells was separated therefrom.

The separated cells were washed three times in a physiological saline solution and diluted so as to attain $1 \times 10^7$ cells/ml. 24 hours after $1 \times 10^7$ cells/ml of cell suspension were transplanted into a group of 10 mice, 20 mg/kg of G 009 was injected into the muscle, subcutis, under the skin and into the abdominal cavity 10 times every other day and 10 mg/kg was injected into the vein 5 times every other day. A physiological saline solution was also administered 0.1 ml by 0.1 ml to the control group in the same manner. After the lapse of 30 days, weight of solid cancer was measured and compared.

As shown in Table 5, cancerous growth was inhibited regardless of administration routes.

TABLE 5

Comparison of antitumor effects according to the administration routes

| Administration route | Number of mice | Weight of tumor (test group/control) | Inhibition ratio(%) |
|---|---|---|---|
| Muscle | 10 | 0.22/4.46 | 95.1 |
| Subcutis | 10 | 0.28/4.52 | 93.8 |
| Abdomen | 10 | 0.18/4.72 | 96.1 |
| Vein | 10 | 0.21/4.45 | 95.2 |

Experiment 3

Life lengthening effects by G 009 administration

Ehrlich ascite tumor cells (EAT) were used to measure the antitumor activity of G 009 in the living body of mice. $1 \times 10^6$ and $5 \times 10^7$ cells/ml of EAT were injected into the abdominal cavity. After the lapse of 24 hours, G009 was dissolved in a phosphate buffer solution and 100 mg/kg thereof was administered into the abdominal cavity and mouth for 12 consecutive days. Then, the average span of life for 20, 25, 30, 40 and 50 days was measured.

The same amount of physiological saline solution was administered to the control group at the same time.

As shown in Table 6, administration of G 009 into the abdominal cavity and vein produced a similar antitumor effect.

TABLE 6

Life lengthening effects by G 009 administration

| | Dose (cells/ml) | Number of mice | Survival rate(%) during observing days after transplantation of cancer cells | | | | |
|---|---|---|---|---|---|---|---|
| | | | 20 | 25 | 30 | 40 | 50 |
| control | $1 \times 10^6$ | 10 | 100 | 40 | 10 | 0 | 0 |
| abdominal | $1 \times 10^6$ | 10 | 100 | 100 | 80 | 70 | 70 |
| intravenous | $1 \times 10^6$ | 10 | 100 | 90 | 70 | 60 | 60 |
| control | $5 \times 10^7$ | 10 | 100 | 30 | 0 | 0 | 0 |
| abdominal | $5 \times 10^7$ | 10 | 100 | 60 | 30 | 20 | 20 |

Experiment 4

Anticancer effects of G 009 in mice treated with trypan blue

G 009 was transplanted into the abdominal cavities of 20–25 g ICR male mice at intervals of one week and successively transferred sarcoma-180 cells were used as experimental tumor cells. The sarcoma-180 cells cultured for 7 days in the abdominal cavity were taken together with abdominal ascites. It was centrifugally separated by 4000 rpm for 5 minutes after adding thereto a sterile saline solution chilled with ice and a precipitate of cells was separated therefrom. The separated cells were washed three times in a physiological saline solution and diluted so as to attain $1 \times 10^7$ cells/ml and 0.1 ml was injected into the left inguinal region using a hypodermic needle.

After the lapse of one day, 4 mg/kg (0.4 ml) of trypan blue was administered into the abdominal cavity. Again, after the lapse of one day, 1 mg/mouse (0.1 ml) of trypan blue as injected hypodermically at a time at intervals of three days so as to amount to a total of 13 mg/mouse.

Immediately after administration of trypan blue, 10 mg of G 009 was injected into the vein. Into the control group a physiological saline solution was injected instead of G009. Both control group and test group were comprised of 10 mice respectively. 30 days after transplantation of tumors, mice were killed and the weight of tumors was measured. Results of this experiment conducted for antitumor effects of G009 in mice treated with trypan blue are shown in Table 7. These results reveal that G 009, a component extracted according to the present invention, activates macrophages associated with antitumor effects by the treatment of mice with trypan blue, a macrophage deactivating factor and that G 009 produces an antitumor effect by activating the function of macrophage together with the antitumor activity of T-lymphocyte.

TABLE 7

Anticancer effects of G 009 on mice treated with trypan blue.

| Group | weight of tumor(g) (Mean ± S.E) |
|---|---|
| Control group | 4.54 ± 0.26 |
| Group treated with G 009 | 0.14 ± 0.05 |
| Group treated with trypan blue | 4.81 ± 0.19 |
| Group treated with G 009 and trypan blue | 2.69 ± 0.17 |

Experiment 5

Effects produced when G 009 is administered into a newborn mouse and the mouse is treated with antithymic globulin after thymectomy The thymectomy of a 2-day old ICR mouse was conducted according to Sjodin's method the cell suspension of sarcoma-180 was transplanted into the inguinal region of the mouse 0.1 ml by 0.1 ml concentrating it to $1 \times 10^7$ cells/ml after the lapse of 6 weeks from thymectomy.

After the lapse of 24 hours from transplantation, 20 mg/kg of G 009 was injected into the muscle 10 times every other day. In order to prevent infection of mice which had thymectomy, water containing tetracycline-HCl was provided. An antithymic serum was separated according to Tadakuma's method. Thymic cells were separated by dissecting the thymus from 1 2- or 3-week old mouse and made into cell suspension by dispersing it in a phosphate buffer solution.

Then, $1 \times 10^6$ cells/ml of thymic cells were injected into the vein of a rabbit three times at intervals of three weeks for immunization. After the lapse of one week from the last injection, antithymic serum was taken and deactivated for 30 minutes at 56° C.

After the fraction of IG G (immunoglobulin G) was separated from the deactivated antithymic serum by precipitating it with ammonium sulphate, 0.1 ml thereof was injected for 10 days into the abdominal cavity of a mouse which passed one day after $1 \times 10^7$ cells/ml of sarcoma-180 was inoculated.

As to G009, 20 mg/kg was injected into the muscle 5 times every other day after the lapse of one day from the transplantation of sarcoma-180.

As shown in Table 8 below, an antitumor effect produced by G 009 in connection with the function of T-cell was remarkably lower on the thymectomized mouse than on the control group and an antitumor effect produced by G009 on the group treated with antithymic globulin was reduced more than on the control group, a group pseudo-treated with normal rabbit globulin.

Thus, the results of these experiments are considered to reveal that G 009 produces an antitumor effect by activating the function of T-cells.

TABLE 8

Comparison of antitumor effects produced by administration of G009 after transplantation of sarcoma-180 into a newborn mouse whose thymus is resected (Experiment 1) and into a mouse treated with antithymic globulin (Experiment 2).

| | Treatment by kind | Number of mice | Dose (mg/Kg) | Wt. of tumor (Mean ± S.E) | Inhibition ratio (%) |
|---|---|---|---|---|---|
| Experiment 1 | N.M | 10 | — | 4.75 ± 0.37 | — |
| | G 009 | 10 | 20 × 10 | 0.18 ± 0.06 | 96 |
| | T.M | 10 | — | 3.55 ± 0.55 | 25 |
| | G 009 | 10 | 20 × 10 | 2.70 ± 0.07 | 43 |
| Experiment 2 | N.M | 10 | — | 5.40 ± 0.31 | — |
| | G 009 | 10 | 20 × 5 | 0.25 ± 0.04 | 95 |
| | A.T.M | 10 | — | 3.78 ± 0.59 | 30 |
| | G 009 | 10 | 20 × 5 | 3.16 ± 0.59 | 41 |
| | N.R.G.M | 10 | — | 3.26 ± 0.61 | 39 |
| | G 009 | 10 | 20 × 5 | 1.20 ± 0.10 | 77 |

*N.M: Normal mouse
T.M: Mouse the thymus of which was resected
A.T.M: Mouse treated with antithymic globulin
N.R.G.M: Mouse treated with normal rabbit globulin

Experiment 6

Effects produced by G 009 on the complement system

Guinea pig sera and fresh human sera were used as the source of complement. Sheep's red blood cells were used as red blood cells. Antisheep-hemolysin as used as an antibody. An experiment on activating the complement was made as follows:

150 ml of a gelatin veronal buffer solution ($GVB^{2+}$) and 50 μl of a sample were put into a test tube, and 50 μl of the complement (100 units/ml) was added thereto.

After it was made to react for 30 minutes at 37° C., the concentration of complement was adjusted to 1 unit/ml by adding $GVB^{2+}$ thereto.

After sheep's red blood cells sensitized in hemolysin (2 MHU/ml) were added in 2 ml to these mixtures and 1.0, 1.2, 1.6 units were added respectively to the complement mixture adjusted with $GVB^{2+}$ solution, the total quantity was adjusted so as to amount to 5 ml with $GVB^{2+}$.

The absorbance of a supernatant solution obtained through centrifugal separation for 5 minutes by 2500 rpm after reaction for 60 minutes at 37° C. was measured at 541 nm. The degree of activity was the amount of the complement consumed by the control group and G 009.

As shown in Table 9, the amount of the complement consumed represented an increase in proportion to the concentration of G 009. Such an increase can be considered to reveal that G 009 increases immunity by activating the function of the complement which is one of the important protective functions of immune system.

TABLE 9

Effects of G 009 on the activation of the complement system

| | conc (μg/ml) | Amount of the consumed complement(%) (Mean ± S.D) |
|---|---|---|
| G 009 | 10 | 15.2 ± 0.59 |
| | 50 | 27.9 ± 0.43 |
| | 100 | 36.4 ± 0.1 |
| | 200 | 45.5 ± 0.3 |
| | 600 | 52.2 ± 0.7 |

Experiment 7

Effects produced by G 009 on the weight of organs associated with immunity

After the lapse of 5 days from intravenous injection of G 009 into the veins of mice in a dosage amounting to 10 mg/kg, the lungs, the livers and the spleens were taken out and their weight was measured. Lysozyme was reacted with *Streptococcus lysodekticus* dissolved in a phosphate buffer solution (pH 6.2) as a substrate and its activity was measured by absorbance at 660 nm.

As shown in Table 10, the reason that the weight of the spleen and the degree of activity of lysozyme registered an increase in the group treated with G 009 was that G 009 activated macrophage and the activity value of lysozyme was thereby made to register an increase.

TABLE 10

Effects of G 009 administration on the activity value of serum enzyme and on the weight of organs

| | Number of mice | Weight (g) | Liver (%) | Spleen (%) | Lungs (%) | Lysozyme (μg/ml) |
|---|---|---|---|---|---|---|
| None | 10 | 24.8 ± 1.0 | 6.54 ± 0.12 | 0.37 ± 0.01 | 0.56 ± 0.02 | 8.75 ± 0.23 |
| G 009 | 10 | 24.5 ± 1.2 | 6.60 ± 0.21 | 0.42 ± 0.04 | 0.54 ± 0.07 | 10.01 ± 0.48 |

*Weight of each organ is a relative value to the weight of a mouse.

Experiment 8

Effects of G 009 on the number of hemolytic plaque forming cells 1). A group of 5 ICR male mice weighing 20–25 g was used as laboratory animals and a sample concentrated to 20 mg/kg was injected into their abdominal cavities for 5 consecutive days. After the lapse of 7 days from the last administration, they were immunized by injecting sheep's red blood cells into their abdominal cavities at a concentration of $1 \times 10^6$ cells/ml. Then, the spleen was taken out 4 days after sheep's red blood cells were administered thereinto.

The spleen cells were extricated by triturating the spleen with a blender together with an equilibrium salt solution chilled with ice. The extricated spleen cells were suspended in a 0.83% ammonium chloride solution and left as they were for 3 minutes at 37° C. to remove a supernatant solution through centrifugal separation for 5 minutes by 2000 rpm. Those cells were again suspended in the equilibrium salt solution chilled with ice through centrifugal separation and the number of the spleen cells was measured with a hemocytometer. 2). The sheep's red blood cells suspended in Alser's solution (20.5 g of glucose, 4.2 g of sodium chloride and 8.0 g of sodium citrate were dissolved in 1 liter of distilled water and used by filtering it with a millipore fiter (0.45 μm)) were washed four times in the equilibrium salt solution for 5 minutes by 2000 rpm and suspended in the same solution so as to amount to 10% in final concentration. 3). A basement plate was made by pouring 10 ml of 1.5% agar (Noble agar, Difco) into a petri dish. Again, 100 μl of 1) and 100 μl of sheep's red blood cells of 2) were mixed into 2 ml of 0.7% agar and poured into the petri dish to attain uniform spread. After it was sensitized for 60 minutes at 37° C., moisture-absorbed guinea pig serum was diluted ten fold with an equlbrium salt solution as the complement and 2.5 ml was added to the plate and cultured for 30 minutes at 37° C. Then, the number of formed hemolytic plaque forming cells and the number of hemolytic plaque forming cells among all spleen cells (PFC/spleen) were calculated.

As shown in Table 11 below, G 009 causes the number of spleen cells and the number of hemolytic plaque forming cells to increase remarkably. Thus, G 009 is considered to be associated with an immunostimulating action.

TABLE 11

Effects of G 009 on hemolytic plaque forming cells in the spleens of mice immunized with sheep's red blood cells

| | Noumber of mice | Number of spleen cells ($1 \times 10^7$) | PFC/the spleen cells ($1 \times 10^6$) |
|---|---|---|---|
| Control | 5 | 38.6 ± 2.1 | 24.4 ± 11.2 |
| G 009 | 5 | 42.6 ± 0.11 | 51.0 ± 14.5 |

Experiment 9

Immunostimulating action

Each group comprises 10 mice. 6-week old, 20–25 g, male, ICR mice were used. G 009 was dissolved in a physiological saline solution and 0.2 ml of solution by concentration was administered into their abdominal cavities. 24 hours later, 0.2 ml of carbon suspension manufactured by mixing 1 ml of perikan drawing ink 17 black and 2 ml of physiological saline solution was injected into the veins of their tails. Then, at 1, 5, 10 and 15 minutes, 0.02 ml of blood was taken from the orbit of an eye with a hematocrit capillary tube coated with heparin and immediately diluted and hemolyzed with 1.6 ml of an aqueous solution of sodium carbonate. The absorbance of this solution was measured at 675 nm and a phagocytosis index (K value) was measured according to Halpern et al's equation. In the control group, 0.2 ml of physiological saline solution was administered to the mouse.

$$K = \frac{\log C_o - \log C}{t - t_o}$$

In the above equation, $C_o$ is the content of carbon powder in blood at time $t_o$.

C is the content of carbon powder in blood at time t.

Results of these experiments are shown in Table 12 below. An index (K) of immunophagocytosis was registered high in proportion to the concentration of G 009. According to those results, G 009 appears most likely to produce an immunostimulating effect by playing a part in immunoresponse.

TABLE 12

Effects of G 009 on immunostimulating action.

|  | Dose (mg/Kg) | Number of mice | Index of phagocytosis (K) (Mean ± S.E) |
|---|---|---|---|
| control | saline solution | 10 | 0.0391 ± 0.003 |
| G 009 | 5 | 10 | 0.1109 ± 0.025 |
|  | 20 | 10 | 0.1453 ± 0.022 |
|  | 50 | 10 | 0.1643 ± 0.008 |
|  | 100 | 10 | 0.1845 ± 0.011 |

Experiment 10

Toxicity test of G 009

Acute toxicity testing of G 009 was conducted on mice, rats and rabbits and results thereof were measured after the lapse of 14 days from administration of G 009.

As shown in Table 13 below, there was no mortality found through routes and species. Therefore, G 009 is a safe material remarkable low in toxicity.

TABLE 13

Results of toxicity test of G 009

| Tested animal | Number of mice | Dose (mg/Kg) | Route | Mortality | Maximum allowance (mg/kg) |
|---|---|---|---|---|---|
| Mouse | 10 | 100–300 | i.v | 0 | >300 |
|  | 10 | 50–2000 | i.p | 0 | >2000 |
|  | 10 | 50–100 | i.m | 0 | >100 |
|  | 10 | 1000–2000 | s.c | 0 | >2000 |
| Rat | 10 | 100–300 | i.v | 0 | >300 |
|  | 10 | 500–1000 | i.p | 0 | >1000 |
|  | 10 | 50–100 | i.m | 0 | >100 |
|  | 10 | 500–1000 | s.c | 0 | >1000 |
| Rabbit | 10 | 100–200 | i.v | 0 | >200 |
|  | 10 | 100–200 | i.p | 0 | >200 |
|  | 10 | 25–50 | i.m | 0 | >50 |
|  | 10 | 50–100 | s.c | 0 | >100 |

Experiment 11

Comparison of characteristics between the species

In order to ascertain the phylogenetic classification and physiological genetic differences of four kinds of type strains (retained by Bacteria 2 section, Agricultural Technology Institute, Office of Rural Development) found excellent as the result of a search made for an antitumor effect produced by those Ganoderma lucidum strains collected in various areas of the country, the following experiments were conducted.

Experimental materials and methods:

Used strains, culture medium and culture

The strains used for the present experiment were four strains found excellent in antitumor effect among those Ganoderma lucidum isolates which grew naturally in the country and the places of collection are shown in Table 14.

Extraction of a sample

The mycelia obtained by centrifugal separation of those cultured in liquid were washed three times in a phosphate buffer saline solution (pH 7.5)n and treated with supersonic waves for 30 seconds under ice-cooling.

After centrifugal separation at 12000 xg, its supernatant solution was used as a sample for electrophoresis.

Quantification of proteins

Proteins in sample were quantified with bovine serum albumin (BSA) used as a type material and by using a protein assay reagent (Pierce Co.).

Electrophoresis

A discontinuous buffer system was used for electrophoresis. Separating gel as prepared by concentrating it to 10% C. 10% T in 240 nM Tris-Cl buffer solution (pH 8.48) and stacking gel was prepared by concentrating it to 3.125% T and 20% C in a Tris buffer solution (30.5 mM Tris, 0.064N $H_3PO_4$, pH 6.9).

In order to solidify these gels, TEMED and ammonium persulfate were used. As running buffers, 40 mM Tris-glycine buffer solution (pH 8.8) was used at anode and 60 mM Tris-Cl buffer solution (pH 7.47) was used at cathode. 70 ug of the sample was developed for 2 hours with 100 V at 4° C. by loading it on the gels.

Gel staining (1). Esterase (E.C. 3,1,1,1)

The developed gels were incubated in 0.2M phosphate buffer solution (pH 6.5) for 30 minutes. While those gels were being incubated, said solution was replaced for a new solution three times. After the activity of incubated gels was adjusted, a color developing solution (α-naphthylacetate 20 mg, ethylene glycolmonoethyl ether 2 ml, fast blue RR sale 20 mg, 0.2M phosphate buffer 120 ml) was added thereto and agitated at 35° C. in a dark place for color development.

(2). Acid phosphatase (E.C. 3,1,3,2)

After activity in gel was adjusted by incubating it in 0.1M acetate buffer solution (pH 5.2), a color developing solution (10% $NgCl_2$ solution 6 ml, fast garnet GBC salt 70 mg, α-naphthylphosphate 80 mg, β-naphthylphosphate 40 mg, 0.1M acetate buffer 100 ml) was added thereto for color development for 30 minutes at 37° C.

(3). Leucine amino peptidase (E.C. 3,4,11,1)

A color developing solution (L-leucyl-62-naphthylamide HCl 20 mg, fast blue K salt 20 mg, distilling water 50 ml, 0.2M Tris-malate buffer (pH 5.4) 120 ml) was added to the gels for color development for 30 minutes in a dark place.

(4). Peroxidase (E.C. 1,11,1,7)

After the gels were washed in water, a color developing solution (Benzidine 1%, acetic acid 9 ml, mixed solution of 1 part of benzidine solution mixed with 40 ml of distilled water, 1 part of 0.03% $H_2O$ and 4 part of distilled water) was added thereto for color development in the dark place.

Results of these experiments were as follows:

Isoenzyme pattern of esterase

As to the esterase band of Ganoderma lucidum, 17 bands came forth in all as shown in FIG. 1. The 5th and 15th bands were common to all strains. The esterase pattern of type strains Fr 07004, Fr 07008 and IY 005 were very similar to one another but the esterase pattern of IY 009 and IY 010 were greatly different from others.

Isoenzyme pattern of acid phosphatase

Figure 5:
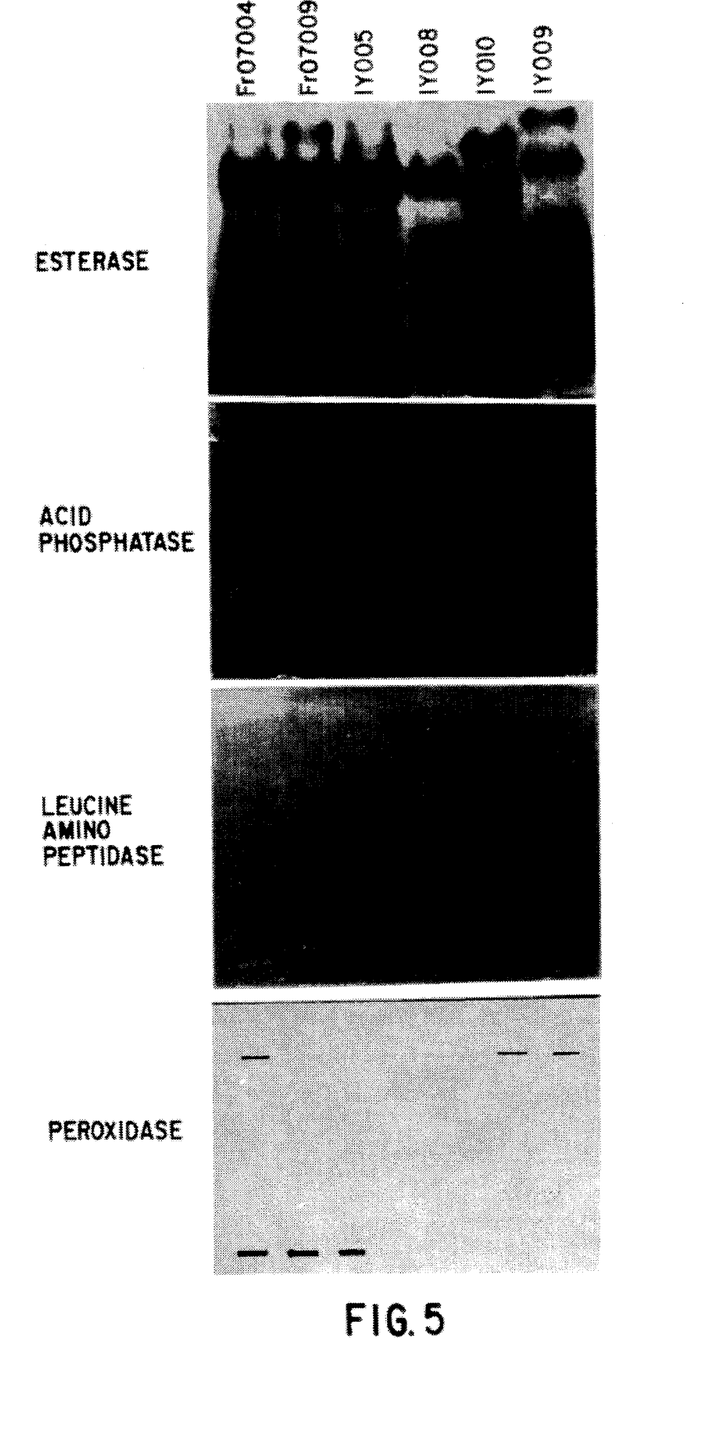
FIG. 5 is a diagram drawn to compare the specificity of a strain IY 009 according to the present invention.

As shown in FIG. 5, the acid phosphatase pattern of type strains Fr 07004, Fr 07008 and IY 005 were very similar to one another but IY 009 and IY 010 showed a different band pattern from others.

Isoenzyme pattern of leucine amino peptidase

From Ganoderma lucidum 3 leucine amino peitidase bands came forth in all. Although those type strains Fr 07004, Fr 07008 and IY 005 showed the same pattern for the most part, IY 009 showed a pattern entirely different from them (FIG. 5).

Isoenzyme pattern of peroxidase 2 peroxidase bands came forth from the strain of Ganoderma lucidum and there was a great affinity among type strains Fr 07004, Fr 07008 and IY 005(FIG. 5).

Affinity between the species

As shown in Table 15, an affinity between type strains Fr 07008 and IY 005 represented 93.8% and an affinity between type strain Fr 07004 and IY 005 showed 82.4%, but an affinity between Fr 07004 and IY 010 and between Fr 07004 and IY 009 registered 30.4% and 31.8%.

According to the above results, a difference of isoenzyme pattern in the same species was made due to a biochemical variation caused by a genetic mutation resultant from a difference of geographical environment and such a difference seemed most likely to be associated with the fact that every strain creates a proteoglycan different in antitumor activity.

TABLE 14

Areas wherein those strains used for the present experiment were collected

| Species | A number of strain | Areas wherein strains were collected | Note |
|---------|-------------------|--------------------------------------|------|
| Ganoderma lucidum | Fr 07004 | Office of Rural Development | Type strain |
| | Fr 07008 | Office of Rural Development | Type strain |
| | IY 005 | Kwangnung, Kyung-gi Province | |
| | IY 008 | Dooryoon Mountains, South Cholla Province | |
| | IY 009 | Dooryoon Mountains, South Cholla Province | |
| | IY 010 | Chiak Mountains, Kangwon Province | |

TABLE 15

Comparison of an affinity between the strains of *Ganoderma lucidum* according to the pattern esterase, leucine amino peptidase and peroxidase

| Species | A number of strain | Affinity (%) | | | | | |
|---------|-------------------|-----|-----|-----|-----|-----|-----|
| | | FR 07004 | Fr 07008 | IY 005 | IY 008 | IY 010 | IY 009 |
| Ganoderma lucidum | Fr 07004 | * | 77.8 | 82.4 | 62.5 | 30.4 | 31.8 |
| | Fr 07008 | | * | 93.8 | 45.0 | 32.8 | 25.0 |
| | IY 005 | | | * | 45.0 | 31.8 | 25.0 |
| | IY 008 | | | | * | 27.3 | 40.0 |
| | IY 010 | | | | | * | 25.0 |
| | IY 009 | | | | | | * |

What is claimed is:

1. A process for preparing a proteoglycan, which comprises:
    i) culturing a fungus having all of the identifying characteristics of the strain KCCM-10045;
    ii) incubating mycelia obtained from said culture in NaOH solution, to obtain a mycelia lysate;
    iii) neutralizing said mycelia lysate with acetic acid;
    iv) dialyzing the neutralized mycelia lysate; and
    v) adding ethanol to the dialyzed lysate to obtain the proteoglycan as a precipitate.

2. A process for preparing a proteoglycan according to claim 1 and further comprising
    vi) dissolving the precipitate from step (v) in water;
    vii) applying the solution of step (vi) to a DEAE-cellulose column, and eluting the proteoglycan therefrom with water, to obtain the desired proteoglycan in an elution fraction.

3. A process for preparing a proteoglycan according to claim 2 and further comprising:
    viii) precipitating the proteoglycan from said elution fraction with methanol; and
    ix) collecting said precipitate to obtain the desired proteoglycan.

4. A proteoglycan obtained by the process of claim 1.

5. A proteoglycan obtained by the process of claim 2.

6. A proteoglycan obtained by the process of claim 3.

7. A proteoglycan fraction according to claim 6, wherein said proteoglycan fraction has a composition that is 93% saccharide and 5% protein, wherein said saccharide portion has a monosaccharide composition of about 46% α-glucose, about 41.7% β-glucose, about 8% galactose, about 3.3% α-mannose and about 1.1% fructose.

8. The proteoglycan fraction of claim 7, wherein said proteoglycan fraction has the biological activity of inhibiting the growth of transplanted sarcoma-180 cells in a mouse.

* * * * *